US012784902B2

(12) United States Patent
Griffin

(10) Patent No.: US 12,784,902 B2
(45) Date of Patent: Nov. 3, 2026

(54) PREDICTIVE HEALTHCARE SCHEDULING TO ADJUST PATIENT OUTCOMES

(71) Applicant: Insight Direct USA, Inc., Chandler, AZ (US)

(72) Inventor: Michael Griffin, Wayland, MA (US)

(73) Assignee: Insight Direct USA, Inc., Chandler, AZ (US)

( * ) Notice: Subject to any disclaimer, the term of this patent is extended or adjusted under 35 U.S.C. 154(b) by 237 days.

(21) Appl. No.: 18/647,540

(22) Filed: Apr. 26, 2024

(65) Prior Publication Data

US 2025/0336502 A1 Oct. 30, 2025

(51) Int. Cl.
*G06Q 10/06* (2023.01)
*G16H 40/20* (2018.01)

(52) U.S. Cl.
CPC .................................. *G16H 40/20* (2018.01)

(58) Field of Classification Search
CPC ............................... G16H 40/20; G16H 10/60
See application file for complete search history.

(56) References Cited

U.S. PATENT DOCUMENTS

| | | | |
|---|---|---|---|
| 8,799,010 | B2 | 8/2014 | Kaundinya et al. |
| 9,785,749 | B2 | 10/2017 | Abedini et al. |
| 10,572,817 | B2 | 2/2020 | Kardes et al. |
| 10,636,015 | B2 | 4/2020 | Nagaraj |
| 10,834,249 | B2 | 11/2020 | Nicholls et al. |
| 10,861,597 | B2 | 12/2020 | Norris et al. |
| 10,997,397 | B2 | 5/2021 | Wang et al. |
| 11,224,486 | B2 | 1/2022 | Barral et al. |
| 11,315,678 | B2 | 4/2022 | Souissi et al. |
| 11,322,247 | B2 | 5/2022 | Bullington et al. |
| 11,436,549 | B1 | 9/2022 | Hull et al. |
| 11,501,859 | B1 | 11/2022 | Guillén et al. |

(Continued)

FOREIGN PATENT DOCUMENTS

| | | | |
|---|---|---|---|
| AU | 2004286362 | B2 | 10/2008 |
| CN | 105792731 | A | 7/2016 |

(Continued)

OTHER PUBLICATIONS

Alon Bergman, Guy David, Hummy Song (2023) “I Quit”: Schedule Volatility as a Driver of Voluntary Employee Turnover. Manufacturing & Service Operations Management 25( 4): 1416-1435. (Year: 2023).

*Primary Examiner* — Maroun P Kanaan
(74) *Attorney, Agent, or Firm* — Kinney & Lange, P.A.

(57) ABSTRACT

A method of creating a healthcare employee schedule includes receiving a first plurality of patient health profiles for a first plurality of patients, receiving a first plurality of employee profiles for a first plurality of healthcare employees, creating a first plurality of employee combinations, simulating a first predicted outcome score for each employee combination using a simulator, selecting a first preferred employee combination of the plurality of predicted employee combinations based on the simulated first predicted outcome scores, and scheduling healthcare employees of the first preferred employee combination during the first time period. Each employee combination of the first plurality of employee combinations includes at least two healthcare employees of the first plurality of healthcare employees.

18 Claims, 6 Drawing Sheets

(56) References Cited

U.S. PATENT DOCUMENTS

| | | | | |
|---|---|---|---|---|
| 11,501,875 | B1 | 11/2022 | Kloster et al. | |
| 11,522,998 | B2 | 12/2022 | Bohannon et al. | |
| 11,532,393 | B2 | 12/2022 | Arkoff et al. | |
| 11,562,587 | B2 | 1/2023 | Reicher et al. | |
| 11,600,390 | B2 | 3/2023 | Are et al. | |
| 12,541,734 | B2 * | 2/2026 | Wayne | G06Q 10/067 |
| 2008/0082391 | A1 | 4/2008 | Gomez | |
| 2017/0124526 | A1 | 5/2017 | Sanderford et al. | |
| 2019/0108469 | A1 | 4/2019 | Limaj et al. | |
| 2020/0151634 | A1 * | 5/2020 | Cinnor | G06N 20/00 |
| 2020/0160985 | A1 | 5/2020 | Kusuma et al. | |
| 2020/0411169 | A1 * | 12/2020 | Brown | G06N 20/00 |
| 2021/0279687 | A1 | 9/2021 | Shimura | |
| 2021/0343411 | A1 | 11/2021 | Zhang et al. | |
| 2022/0108790 | A1 | 4/2022 | Rice | |
| 2022/0351846 | A1 | 11/2022 | Bala et al. | |
| 2022/0375583 | A1 * | 11/2022 | Hosny | G16H 50/20 |
| 2023/0011342 | A1 | 1/2023 | Dewan | |
| 2023/0062010 | A1 | 3/2023 | Malboubi et al. | |
| 2023/0073776 | A1 | 3/2023 | Muse et al. | |
| 2023/0073931 | A1 | 3/2023 | Watkins et al. | |
| 2023/0081372 | A1 | 3/2023 | Hartman et al. | |
| 2023/0082014 | A1 | 3/2023 | Bleeker et al. | |

FOREIGN PATENT DOCUMENTS

| | | | |
|---|---|---|---|
| CN | 110570937 | A | 12/2019 |
| CN | 109659017 | B | 9/2020 |
| CN | 110752017 | B | 12/2020 |
| CN | 112530576 | A | 3/2021 |
| CN | 113724823 | A | 11/2021 |
| CN | 114169563 | A | 3/2022 |
| CN | 110232971 | B | 4/2022 |
| EP | 1763837 | A1 | 3/2007 |
| EP | 3702988 | A1 | 9/2020 |
| JP | 6878222 | B2 | 5/2021 |
| JP | 7011339 | B2 | 1/2022 |
| KR | 1020070053235 | A | 5/2007 |
| WO | 1999063462 | A1 | 12/1999 |
| WO | 2023038946 | A1 | 3/2023 |
| WO | 2023039114 | A1 | 3/2023 |

* cited by examiner

PREDICTIVE HEALTHCARE SCHEDULING TO ADJUST PATIENT OUTCOMES

BACKGROUND

The present disclosure relates to worker staffing and allocation and, more particularly, for generating healthcare employee schedules based on employee and patient attributes in order improve patient outcomes.

Medical care involves the prevention, diagnosis, treatment, amelioration, etc. of a disease, condition, injury, or other impairment suffered by a patient, and can involve a combination of care from medical staff, surgical interventions, pharmaceutical interventions, education, hospitalization, etc. The specific medical interventions that a patient receives are selected by decisions of medical staff that provide care to a patient and at least partially drive patient outcomes.

SUMMARY

An example of a method of creating a healthcare employee schedule includes receiving a first plurality of patient health profiles for a first plurality of patients, receiving a first plurality of employee profiles for a first plurality of healthcare employees, creating a first plurality of employee combinations, simulating a first predicted outcome score for each employee combination using a simulator, selecting a first preferred employee combination of the plurality of predicted employee combinations based on the simulated first predicted outcome scores, and scheduling healthcare employees of the first preferred employee combination during the first time period. Each patient health profile of the first plurality of patient profiles corresponds to one patient of the first plurality of patients, where the patients first plurality of patients is expected to visit a healthcare facility during a first time period. Each employee profile for the first plurality of healthcare employees corresponds to one healthcare employee of the first plurality of healthcare employees, where the healthcare employees of the first plurality of healthcare employees belong to a first class of healthcare employees and each employee profile of the first plurality of employee profiles comprises at least one employee attribute. Each employee combination of the first plurality of employee combinations includes at least two healthcare employees of the first plurality of healthcare employees. The predicted outcome scores are simulated a first computer-implemented machine learning model, the first plurality of patient health profiles, and employee profiles of the first plurality of employee profiles corresponding to the healthcare employees of the employee combination. The first predicted outcome score describes a health outcome for the first plurality of patients and the first computer-implemented machine learning model is configured to generate predicted outcome scores based on patient health profiles and employee profiles.

An example of a system includes patient database, an employee database, and an electronic employee scheduling system including a processor and computer-readable memory encoded with instructions. The instructions, when executed, cause the processor to receive a first plurality of patient health profiles from the patient database, receive a first plurality of employee profiles from the employee database, create a first plurality of employee combinations, simulate, a first predicted outcome score using a simulator for each employee combination, select a first preferred employee combination of the plurality of predicted employee combinations based on the simulated first predicted outcome scores, and modify the electronic employee scheduling system to schedule healthcare employees of the first preferred employee combination during the first time period. Each patient health profile of the first plurality of patient profiles corresponds to one patient of the first plurality of patients, where the patients first plurality of patients is expected to visit a healthcare facility during a first time period. Each employee profile for the first plurality of healthcare employees corresponds to one healthcare employee of the first plurality of healthcare employees, where the healthcare employees of the first plurality of healthcare employees belong to a first class of healthcare employees and each employee profile of the first plurality of employee profiles comprises at least one employee attribute. Each employee combination of the first plurality of employee combinations includes at least two healthcare employees of the first plurality of healthcare employees. The predicted outcome scores are simulated a first computer-implemented machine learning model, the first plurality of patient health profiles, and employee profiles of the first plurality of employee profiles corresponding to the healthcare employees of the employee combination, the first predicted outcome score describing a health outcome for the first plurality of patients, where the first computer-implemented machine learning model is configured to generate predicted outcome scores based on patient health profiles and employee profiles.

The present summary is provided only by way of example, and not limitation. Other aspects of the present disclosure will be appreciated in view of the entirety of the present disclosure, including the entire text, claims, and accompanying figures.

Figure 1:
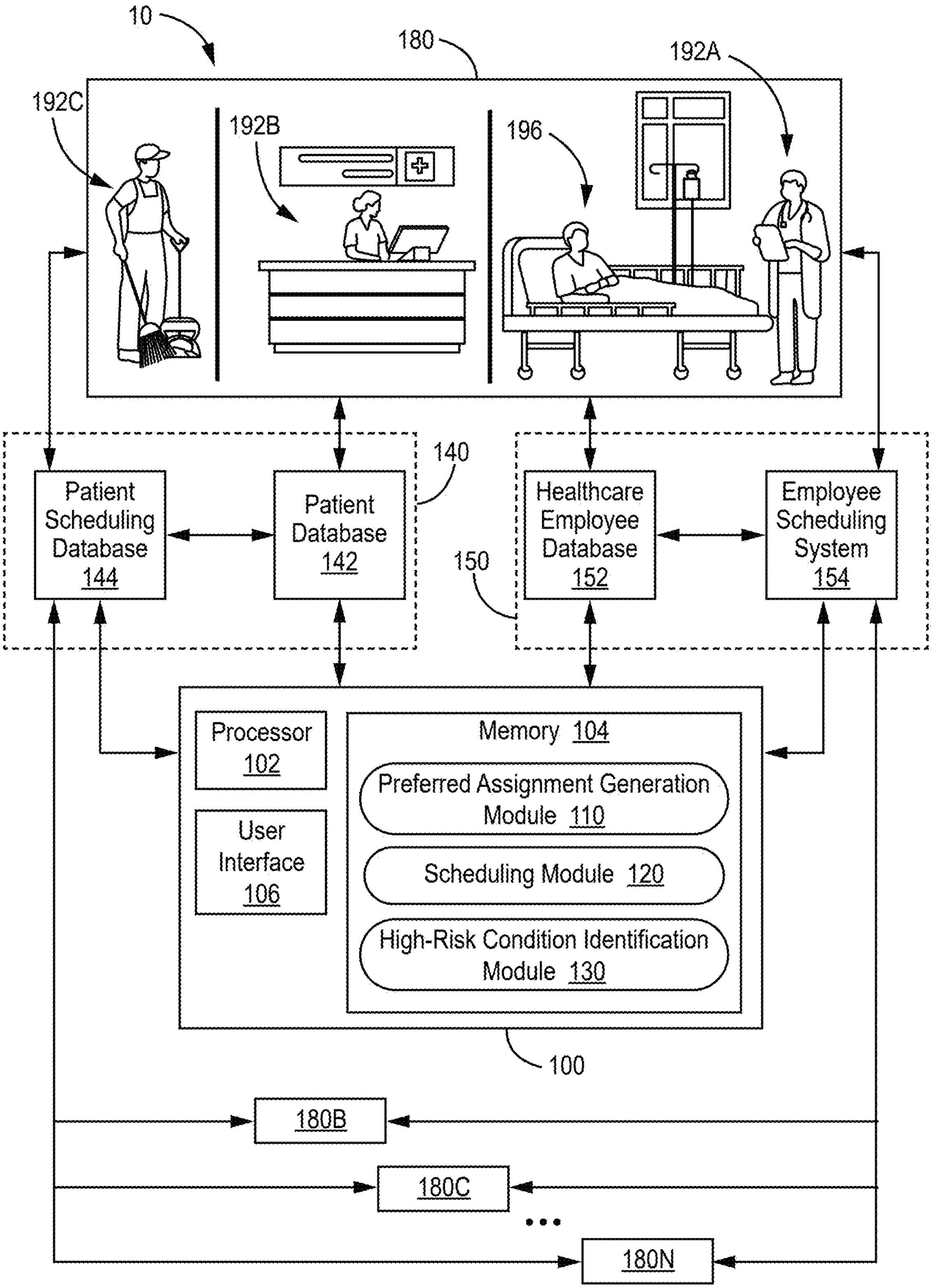
FIG. 1 is a schematic diagram of an example of a scheduling system for scheduling at healthcare facilities.

While the above-identified figures set forth one or more examples of the present disclosure, other examples/embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale, and applications and examples of the present invention may include features and components not specifically shown in the drawings.

DETAILED DESCRIPTION

The present disclosure relates to systems and methods for scheduling healthcare employees. More specifically, the present disclosure relates to systems and methods that schedule healthcare employees according to an expected patient population during a particular time period or shift. As will be explained in more detail subsequently, the present disclosure describes matching schedulers that can calculate predicted patient outcomes for any combination of staff and patients. The matching schedulers described herein can be used to adjust, optimize, and/or improve staffing for an expected patient population in order to adjust and/or improve patient outcomes. As will also be explained in more detail subsequently, the matching schedulers described herein can be used to schedule all employees and/or any type of employee working at a healthcare facility.

The matching schedulers described herein can be used to match medical and non-medical healthcare staff to a group of incoming patients in order to adjust and/or improve patient outcomes for those patients. As used to herein, the terms "medical staff," "medical healthcare staff," and "medical professionals" refer to healthcare employees that perform medical tasks, such as diagnosis, prognosis, treatment, etc. As used to herein, the terms "non-medical staff" and "non-medical healthcare staff" refer to healthcare employees that not typically perform medical tasks and instead typically perform support tasks, such as administrative tasks, maintenance tasks, janitorial tasks, etc. Patient outcomes are driven partially by the training, skill level, and expertise of medical healthcare staff that provide medical advice to the patient. For example, a doctor or a nurse with expertise in a medical issue for which the patient is seeking treatment may provide better treatment for that patient that a doctor or nurse lacking expertise in that medical issue. The personality of the medical professionals interacting with a patient may also influence patient outcomes. For example, if a patient does not find the personality of a particular medical professional to be agreeable, the patient may be less likely to follow medical advice provided by that medical professional. Patient outcomes can also be driven by interactions with staff in non-medical roles, such as administrative or janitorial staff, or staff in other non-medical support roles. For a given visit to a healthcare facility, the interactions a patient has with non-medical staff before, during, and after receiving medical care and/or medical advice from medical staff can significantly impact the patient's overall experience during that visit. For example, the competency, skill level, agreeableness, and/or personality of a staff member may influence a patient's experience in a healthcare facility. Improving patient experience can cause a concomitant improvement in patient attitudes toward medical advice received from medical staff, thereby providing additional improvements to patient outcomes. Improving patient experience can also improve the likelihood that a patient returns to a particular healthcare facility for treatment or care in the future (i.e., patient retention).

FIG. 1 is a schematic diagram of scheduling system 10, which is a system for scheduling healthcare employees and patients at one or more healthcare facilities. Scheduling system 10 includes matching scheduler 100, which includes processor 102, memory 104, and user interface 106. Memory 104 includes patient scheduling module 110, employee scheduling module 120, and rescheduling module 130. Scheduling system 10 also includes patient system 140, which includes patient database 142 and patient scheduling system 144, and employee system 150, which includes healthcare employee database 152 and healthcare employee scheduling system 154. Patient system 140 and employee system 150 can be used to store information describing and create schedules for patients and employees, respectively, at a healthcare facility 180A-N. Healthcare facilities 180A-N belong to a hospital system 182. FIG. 1 also includes an illustrative representation of healthcare facility 180A that depicts healthcare employees 192A-C and patient 196.

Matching scheduler 100 can be used in scheduling system 10 to inspect and analyze incoming patients and available healthcare staff, and to create employee schedules that adjust and/or improve patient outcomes by selecting a combination of healthcare staff having, for example, particular expertise, training, skill levels, personalities, and/or biographical attributes, among other options. As will be explained in more detail subsequently, matching scheduler 100 can be configured to automatically modify employee schedules to adjust and/or improve patient outcomes, and further can be configured to automatically update employee schedules to fill staffing gaps that arise due to unexpected employee absences.

Processor 102 can execute software, applications, and/or programs stored on memory 104. Examples of processor 102 can include one or more of a processor, a microprocessor, a controller, a digital signal processor (DSP), an application specific integrated circuit (ASIC), a field-programmable gate array (FPGA), or other equivalent discrete or integrated logic circuitry. Processor 102 can be entirely or partially mounted on one or more circuit boards.

Memory 104 is configured to store information and, in some examples, can be described as a computer-readable storage medium. Memory 104, in some examples, is described as computer-readable storage media. In some examples, a computer-readable storage medium can include a non-transitory medium. The term "non-transitory" can indicate that the storage medium is not embodied in a carrier wave or a propagated signal. In certain examples, a non-transitory storage medium can store data that can, over time, change (e.g., in RAM or cache). In some examples, memory 104 is a temporary memory. As used herein, a temporary memory refers to a memory having a primary purpose that is not long-term storage. Memory 104, in some examples, is described as volatile memory. As used herein, a volatile memory refers to a memory that that the memory does not maintain stored contents when power to the memory 104 is turned off. Examples of volatile memories can include random access memories (RAM), dynamic random access memories (DRAM), static random access memories (SRAM), and other forms of volatile memories. In some examples, the memory is used to store program instructions for execution by the processor. The memory, in one example, is used by software or applications running on matching scheduler 100 (e.g., by a computer-implemented machine learning model or a data processing module) to temporarily store information during program execution.

Memory 104, in some examples, also includes one or more computer-readable storage media. Memory 104 can be configured to store larger amounts of information than volatile memory. Memory 104 can further be configured for long-term storage of information. In some examples, memory 104 includes non-volatile storage elements. Examples of such non-volatile storage elements can include, for example, magnetic hard discs, optical discs, floppy discs, flash memories, or forms of electrically programmable memories (EPROM) or electrically erasable and programmable (EEPROM) memories.

User interface 106 is an input and/or output device and enables an operator to control operation of matching scheduler 100 and/or other components of scheduling system 10. For example, user interface 106 can be configured to receive inputs from an operator and/or provide outputs regarding driver quantity recommendations. User interface 106 can include one or more of a sound card, a video graphics card, a speaker, a display device (such as a liquid crystal display (LCD), a light emitting diode (LED) display, an organic light emitting diode (OLED) display, etc.), a touchscreen, a keyboard, a mouse, a joystick, or other type of device for facilitating input and/or output of information in a form understandable to users and/or machines.

Matching scheduler 100 is in in electronic communication with patient database 142, patient scheduling system 144, healthcare employee database 152, and employee scheduling system 154. Matching scheduler 100 can access and modify data stored by patient database 142, patient scheduling system 144, healthcare employee database 152, and employee scheduling system 154. For example, matching scheduler 100 can modify schedules stored by patient scheduling system 144 and employee scheduling system 154 to adjust employee and/or patient populations during particular time periods.

Patient database 142 is a database for storing patient health information. Patient database 142 can store patient health information for patients that have visited a healthcare facility 180A-N, are scheduled to visit a healthcare facility 180A-N, may potentially visit a healthcare facility 180A-N, or any combination thereof. Patient database 142 can store information in a patient-by-patient manner and the information for each patient stored by patient database 142 can be referred to as a "patient profile." Patient database 142 can be queryable such that processor 102 can query patient database 142 with identifying information for a particular patient to retrieve the patient health profile for that patient. Patient database 142 can be queried using, for example, identifying information for patients, such as names, identification numbers, etc. A patient health profile can, in some examples, include one or more electronic health records (EHRs). The patient health profile can also, in some examples, include information describing the nature of the patient's visit to the healthcare facility, such as a treatment, diagnostic test, or other intervention that the patient is scheduled or likely to receive. Additionally and/or alternatively, a patient health profile can include personality and/or biographical information for a patient, such as a patient's age, gender, marital status, temperament, or demeanor, among other options. Patient database 142 can be updated by medical staff of a healthcare facility 180A-N and, in some examples, can be connected to a wide area network (WAN; e.g., the Internet) to receive patient health information from a healthcare facility or hospital system outside of and/or unaffiliated with hospital system 182. The information stored by each patient health profile can be referred to as a patient's "patient health attributes" or "patient attributes."

Patient database 142 includes machine-readable data storage capable of retrievably housing stored data, such as database or application data. In some examples, patient database 142 includes long-term non-volatile storage media, such as magnetic hard discs, optical discs, flash memories and other forms of solid-state memory, or forms of electrically programmable memories (EPROM) or electrically erasable and programmable (EEPROM) memories. Patient database 142 can organize data using a relational database management system (RDBMS), object-relational database management system (ORDBMS), columnar database management systems (CDBMS), document-oriented database management systems (DoDBMS) and/or a multi-model database management system (MMDBMS).

Patient scheduling system 144 creates and manages patient appointments at healthcare facilities 180A-N of hospital system 182. Patient scheduling system 144 is connected to patient database 142 and/or matching scheduler 100 such that patient scheduling system 144 can electronically communicate with patient database 142 and/or matching scheduler 100, respectively. Patient scheduling system 144 can be modified by matching schedule 100 and/or can be modified by an employee (i.e., a medical and/or non-medical employee) of a healthcare facility 180A-N. Patient scheduling system 144 can store patient appointment information to computer-readable memory substantially similar to memory 104, and further can include processor(s) and/or user interface(s) substantially similar to processor 102 and user interface 106, respectively. Patient scheduling system can also store information describing maximum, preferred, and/or minimum numbers of patients for each healthcare facility 180A-N and, in some examples, can include maximum, preferred, and/or minimum desired patient counts in a time-resolved manner, such as for particular days or during particular times of day.

Patient database 142 and patient scheduling system 144 together form patient system 140. Although patient database 142 and patient scheduling system 144 are shown as separate elements of patient system 140, in some examples patient database 142 and patient scheduling system 144 can be combined into a single device or instantiated on a single device. In yet further examples, one or both of patient database 142 and patient scheduling system 144 can include multiple devices or be instantiated across multiple devices.

Healthcare employee database 152 is a database for storing information describing employees of healthcare facilities 180A-N. Healthcare employee database 152 can store any suitable information for describing the employees of healthcare facilities 180A-N. Healthcare employee database 152 can store information in an employee-by-employee manner and the data stored for each employee of healthcare facilities 180A-N can be referred to as an "employee profile." Each employee profile includes various attributes that describe an employee. For example, the employee profiles can include preferences regarding shift time and shift location (i.e., preferences regarding work at a particular healthcare facility 180A-N). Additionally and/or alternatively, employee profiles stored by healthcare employee database 152 can include information describing employee expertise, training, education, specialties, skill sets, etc. Each employee profile can also include a descriptor or other information describing a class or general type or group of employees to which an employee belongs. For example, an employee class could designate an employee as a medical employee or a non-medical employee, and/or as a specific type of medical employee or non-medical employee, such as a doctor, a nurse, a janitor, an administrative employee, or any other suitable class or type of employee of the healthcare facility. In some examples, the stored employee profiles can include store biographical information describing each healthcare employee, such as age, marital status, and/or gender information, and/or information describing personality traits of each healthcare employee, such as temperament, demeanor, etc. Healthcare employee database 152 can be queryable such that processor 102 can query healthcare employee database 152 with identifying information for a particular healthcare employee to retrieve the employee profile for that patient. Healthcare employee database 152 can be queried using, for example, identifying information for employees, such as names, identification numbers, etc. Healthcare employee database can be updated medical or non-medical staff of a healthcare facility 180A-N, or another suitable entity, such as a human resources officer of hospital system 182.

Healthcare employee database 152 includes machine-readable data storage capable of retrievably housing stored data, such as database or application data. In some examples, healthcare employee database 152 includes long-term non-volatile storage media, such as magnetic hard discs, optical discs, flash memories and other forms of solid-state memory, or forms of electrically programmable memories (EPROM) or electrically erasable and programmable (EEPROM) memories. Healthcare employee database 152 can organize data using a relational database management system (RDBMS), object-relational database management system (ORDBMS), columnar database management systems (CDBMS), document-oriented database management systems (DoDBMS) and/or a multi-model database management system (MMDBMS).

Employee scheduling system 154 creates and manages employee schedules at healthcare facilities 180A-N of hospital system 182. Employee scheduling system 154 is connected to healthcare employee database 152 and/or matching scheduler 100 such that Employee scheduling system 154 can electronically communicate with healthcare employee database 152 and/or matching scheduler 100, respectively. Employee scheduling system 154 can be modified by matching schedule 100 and/or can be modified by medical or non-medical staff of a healthcare facility 180A-N, or another suitable entity, such as a human resources officer of hospital system 182. Employee scheduling system 154 can store patient appointment information to computer-readable memory substantially similar to memory 104, and further can include processor(s) and/or user interface(s) substantially similar to processor 102 and user interface 106, respectively. In some examples, employee scheduling system 154 can store information describing a preferred number of employees per shift or during a particular time period, and can do so for each healthcare facility 180A-N of hospital system 182. Additionally and/or alternatively employee scheduling system 154 can store information describing how many employees of a particular type or class (e.g., how many doctors, nurses, janitors, etc.) are preferred per shift or during a particular time period, and can do so for each healthcare facility 180A-N of hospital system 182.

Healthcare employee database 152 and patient scheduling system 144 together form employee system 150. Although healthcare employee database 152 and patient scheduling system 144 are shown as separate elements of employee system 150, in some examples healthcare employee database 152 and patient scheduling system 144 can be combined into a single device or instantiated on a single device. In yet further examples, one or both of healthcare employee database 152 and patient database 142 can include multiple devices or be instantiated across multiple devices.

Healthcare facilities 180A-N are physical locations where healthcare is provided. Each of healthcare facilities 180A-N corresponds to a discrete, location, or structure, such that different sets of healthcare employees can be scheduled (i.e., by employee scheduling system 154) to work at different healthcare facilities 180A-N at the same time or substantially at the same time. Healthcare facilities 180A-N belong to hospital system 182. Hospital system 182 is a business or other organization that manages and operates healthcare facilities 180A-N. The employees of hospital system 182 include all employees of healthcare facilities 180A-N as well as various other employees that do not work specifically for a healthcare facility 180A-N, such as employees in managerial or administrative roles and whose normal duties include the performance of tasks for more than one healthcare facility 180A-N.

A healthcare facility 180A-N can be a hospital, clinic, treatment center, or any other suitable type of facility for providing medical advice, diagnosis, prognosis, treatment, etc. Scheduling system 10 provides patient and employee schedules for all of healthcare facilities 180A-N. In some examples, scheduling system 10 can include only one healthcare facility 180A-N and, in yet further examples, scheduling system 10 can include fewer or more than the four healthcare facilities 180A-N depicted in in FIG. 1.

FIG. 1 includes a depiction of healthcare facility 180A, which is shown as including healthcare employees 192A-C and patient 194, as well as various medical, office, facilities, and maintenance equipment. In the depicted example, healthcare employee 192A is a member of medical staff and is interacting with patient 194 in a medical setting. Healthcare employees 192B-C are different classes of non-medical employees. More specifically, healthcare employee 192B is depicted as an administrative staff member and healthcare employee 192C is depicted as a janitorial staff member. The examples provided in FIG. 1 are included for illustrative purposes and, in other examples, healthcare facility 180A or any other facility of hospital system 182 can include other examples of medical and/or non-medical employees. For example, medical staff of a healthcare facility 180A-N can include one or more nurses, one or more care technicians, one or more laboratory technicians, one or more residents or interns, one or more dietitians, one or more pharmacists, or one or more therapists, among other options. Non-medical staff of a healthcare facility 180A-N can include facilities employees, food services employees, transportation and transportation maintenance employees, or another type of support staff.

Patient scheduling module 110 includes one or more programs for scheduling patients to visit a healthcare facility 180A-N. Patient scheduling module 110 is an optional element of matching scheduler 100 and can be omitted in examples where matching scheduler 100 docs not create or suggest patient schedule. In examples lacking patient scheduling module 110, patients can able to schedule appointments with a healthcare facility 180A-N by interacting with a website of hospital system 182 and/or by requesting that an employee of a healthcare facility schedule the appointment, and patient scheduling system 144 can be updated accordingly. In examples having patient scheduling module 110, patient scheduling module 110 can be used to predict times of day that are associated with improved patient outcomes for a given patient. The programs of patient scheduling module 110 can be configured to output those time(s) and/or to automatically schedule the patient for an appointment during those a time period associated with improved patient outcomes by modifying data of patient scheduling system 144. The programs of patient scheduling module 110 can be configured to analyze a patient health profile for a patient to determine one or more periods of time which are associated with improved patient outcomes. Patient scheduling module 110 can, for example, including one or more computer-implemented machine learning models configured to analyze patient health profiles and output scores or values describing patient outcome. The programs of patient scheduling module 120 can be run iteratively to recommend patient appointment times for as many time periods, shifts, and/or appointment windows as is desirable for a given healthcare facility 180A-N and/or for hospital system 182.

Employee scheduling module 120 includes one or more programs for scheduling employees to work at a healthcare facility 180A-N. The program(s) of employee scheduling module 120 can be used to analyze patient health profiles from patient database 142 and employee profiles from healthcare employee database 152 and to create scores or values that describe expected outcomes for patients with different combinations of employees. As referred to herein, a "patient outcome score" is a score that describes the positivity of the expected outcome of a particular visit to a healthcare facility. As described previously, the patient outcome score can be influenced by patient experience in the healthcare facility and, accordingly patient experience can be used to build and/or train models to predict expected patient outcomes. In some examples, employee scheduling module 120 can include one or more trained computer-implemented machine learning models trained to output patient outcome scores for combinations of one or more patients and one more healthcare employees. The program (s) of employee scheduling module 120 can also be used to select a preferred employee combination for a given combination of patients according to the patient outcome scores.

The program(s) of employee scheduling module 120 can be configured to request identifying information for all patients visiting a healthcare facility 180A-N during a particular time period from patient scheduling system 144 and further to request identifying information for all employees available to work during that time period from employee scheduling system 154. The program(s) of employee scheduling module 120 can query patient database 142 with the patient identifying information to receive patient profiles for the patients scheduled during the time period, and further can query healthcare employee database 152 to receive employee profiles for each available employee. The program(s) of employee scheduling module 120 can be further configured to create a plurality of employee combinations of the available employees. The program(s) of employee scheduling module 120 can be configured to only include certain numbers of particular classes of healthcare employees in each combination and, further, can be configured to request and receive preferred staffing quantities for each class of healthcare employee from employee scheduling system 154 or another element of scheduling system 10.

The program(s) of employee scheduling module 120 can then score each employee combination using one or more scoring programs, such as the computer-implemented machine learning model described previously, based on the patient profile information for all patients scheduled during the time period and the employee profile information for the employees of each employee combination. The program(s) of employee scheduling module 120 can be configured to score employee combinations by, for example, scoring each employee combination for each patient, and summing the totals for each employee combination. The summed scores for each employee combination can then be compared and the employee combination producing the greatest score can be selected to be scheduled during the time period. In some examples, the program(s) of employee scheduling module 120 can be configured to select the employee combination producing the highest score that also does not produce an individual patient outcome scores below a pre-determined threshold, thereby excluding employee combinations that overly favor certain incoming patients at the expense of care of other of the incoming patients during the time period. The threshold can be based on, for example, likelihood of patient mortality or injury or likelihood of healthcare facility liability at particular patient outcome scores. In yet further examples, the scoring algorithm (e.g., the computer-implemented machine learning model) can be configured to output a single score that describes an expected patient outcome for a group of patients.

After selecting a preferred employee combination for the patients scheduled during the time period, the program(s) of employee scheduling module 120 can be configured to output the preferred employee combination and/or to modify employee scheduling system 154. The program(s) of employee scheduling module 120 can output the preferred employee combination to allow employees of hospital system 182 to schedule the employees of the employee combination. Additionally and/or alternatively, the program(s) of employee scheduling module 120 can be configured to automatically modify employee scheduling system 154 to schedule the employees of the preferred employee combination. The programs of employee scheduling module 120 can be run iteratively to create employee schedules for as many time periods, shifts, and/or appointment windows as is desirable for a given healthcare facility 180A-N and/or for hospital system 182.

Rescheduling module 130 includes one or more programs for scheduling employees to work at a healthcare facility 180A-N to fill in for the loss of a previously-scheduled employee during a shift. For example, an employee may call out sick prior to a shift, may quit their employment with the healthcare facility 180A-N and/or hospital system 182, and/or may otherwise become unexpectedly unavailable to work during a previously-scheduled shift. The program(s) of rescheduling module 130 can be used to schedule or reschedule an employee to work during the understaffed shift.

The program(s) of rescheduling module 130 can query employee scheduling system 120 to determine available employees during the understaffed shift of the same class or type (i.e., who perform the same duties) as the absent employee in order to receive identifying information for the available employees. The program(s) of rescheduling module 130 can then query employee database 154 to receive employee profiles for those employees. Similarly, the program(s) of rescheduling module 130 can query patient scheduling system 142 to receive patient identifying information for the patients scheduled during the understaff shift and, subsequently, query patient database 144 to receive patient profile information for those scheduled patients. The program(s) of rescheduling module 130 use the same scoring algorithm (e.g., the same computer-implemented machine learning model) to score the replacement employees as used by scheduling module 120, and the employee producing the greatest patient outcome score can be selected as the preferred replacement employee.

In some examples, there may not be available replacement employees that are not already scheduled during the understaffed shift. If no unscheduled employees are available to replace the understaffed employee, the program(s) of rescheduling module 130 can be configured to query employee scheduling system 152 to obtain a list of employees who belong to the same class of employee as the absent employee and also who are scheduled during the understaffed shift to work at a different healthcare facility 180A-N than the location of the understaffed shift or who are scheduled to work a different shift at the same healthcare facility having the understaffed shift. The program(s) of rescheduling module 130 can then obtain employee profiles for that limited pool of already-scheduled employees by querying employee database 152. These employees are referred to herein as "potential transfer employee."

The program(s) of rescheduling module 130 can be configured to score each potential transfer employee using patient profile information for patients that would be visiting during the understaffed shift, but can also be configured to retrieve patient information for the healthcare facility 180A-N for patients scheduled during the potential transfer employee's original shift and create a patient outcome score for those patients that describes the predicted impact of the potential transfer employee on the care those patients will receive. The program(s) of rescheduling module 130 can compare the impact of removing the potential transfer employee from the potential transfer employee's originally-scheduled shift and the impact of adding the potential transfer employee to the understaffed shift. The program(s) of rescheduling module 130 can use, for example, one or more optimization algorithms to select a preferred replacement employee or, in other examples, can select the preferred replacement employee the employee having the greatest difference between the two calculated patient outcome scores.

After selecting the preferred replacement employee, the program(s) of rescheduling module 130 can be configured to output the preferred replacement employee and/or to modify employee scheduling system 154. The program(s) of rescheduling module 130 can output the preferred replacement employee to allow employees of hospital system 182 to schedule the preferred replacement employee to work the understaffed shift. Additionally and/or alternatively, the program(s) of rescheduling module 130 can be configured to automatically modify employee scheduling system 154 to schedule the preferred replacement employee during the understaffed shift. The program(s) of rescheduling module 130 can be configured to run iteratively and/or in specified intervals of time in order to promptly reschedule employees to cover understaffed shifts.

Advantageously, matching scheduler 100 allows for the employees working during a particular shift, time period, or appointment window at a hospital 180A-N to be selected according to attributes of the patients scheduled or expected to visit during that particular shift, time period, or appointment window in order to adjust and/or improve patient outcomes. Notably, matching scheduler not only allows for medical staff, such as doctors or nurses, to be selected to adjust and/or improve patient outcomes, but also allows for non-medical staff, such as administrative or janitorial staff, to be selected to adjust and/or improve patient outcomes. Matching scheduler 100 further allows employee schedules to be modified automatically to reduce labor required to create employee schedules and, in some examples, patient appointment times and/or windows. Matching scheduler 100 can be used to create employee schedules for all employees of a healthcare facility or can be used to create schedules for any subset of employees of a healthcare facility. For example, matching scheduler 100 can be used to create employee schedules for only employees that are doctors, nurses, administrative employees, etc., or any combination thereof. The manner in which matching scheduler 100 adjusts and/or improves patient outcomes can also cause improvements to patient experience, which can increase patient retention, as described previously.

Further, matching scheduler 100 be formed as a separate hardware device that can be communicatively connected to an existing employee system 150 and/or an existing patient system 140 (as is depicted in FIG. 1), and/or can be implemented as software on an existing employee system 150 and/or an existing patient system 140. [Advantageously, this allows the advantages of matching scheduler 100 to be implemented in existing healthcare facilities with substantially little reconfiguration of existing electronic hospital management software and/or systems. In other examples, new scheduling systems that integrate or substantially integrate the components depicted in FIG. 1 of matching scheduler 100, employee system 150, patient scheduling system 140, or any combination thereof can be created and provide the advantages of matching scheduler 100 discussed herein.

Figure 2:
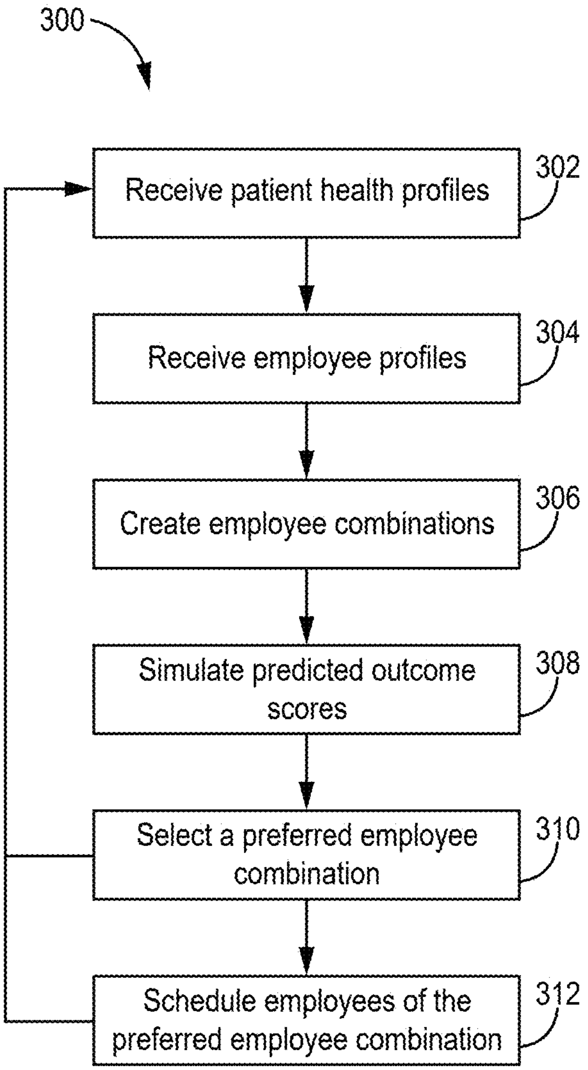
FIG. 2 is a flow diagram of an example of a method of scheduling healthcare employees suitable for use by the system of FIG. 1

FIG. 2 is a flow diagram of method 300, which is a method of creating healthcare employee schedules. Method 300 includes steps of receiving patient health profiles (step 302), receiving employee profiles (step 304), creating employee combinations (step 306), simulating predicted outcome scores (step 308), selecting a preferred employee combination (step 310), and scheduling employees of the preferred employee combination (step 312). Method 300 can be performed by matching scheduler 100 to schedule employees of hospital system 182 and/or any healthcare facility 180A-N. Method 300 allows for any population of employees of a healthcare facility 180A-N to be scheduled to match an incoming group of patients in order to adjust, improve, and/or optimize the predicted health outcomes for those patients. Method 300 will be discussed generally herein with reference to matching scheduler 100 for simplicity and clarity, but method 300 can be performed by any suitable hardware device to create employee schedules for a healthcare facility. Method 300 is performable by, for example, one or more programs of employee scheduling module 120.

In step 302, matching scheduler 100 receives patient health profiles. The patient health profiles correspond to the patients that are expected to visit a healthcare facility during a particular time period and describe various information about the patients. The patient profiles can include the information described previously in the discussion of FIG. 1, such as the nature of the patient's visit to the healthcare facility (e.g., the type of treatment, diagnostic produce, etc. that the patient expects to receive), the patient's health history, biographical information describing the patient, etc. The time period can be selected to be, for example, a typical shift at the healthcare facility. In other examples, the time period can be any suitable length of time for creating employee schedules. Matching scheduler 100 can receive the patient health profiles from patient database 142 by, for example, querying patient database 142 with identifying information for patients scheduled to visit during the time period. Matching scheduler 100 can query patient scheduling system 144 to obtain patient identifying information (e.g., a list of patient names) for patients scheduled to visit the healthcare facility during the time period.

In step 304, matching scheduler 100 receives employee profiles. The employee profiles can include the information described previously in the discussion of FIG. 1, such as employee expertise, training, education, specialties, skill sets, biographical information, temperament, personality, etc. The employee profiles describe employees available to work during the time period. Employee availability can be determined based on, for example, information stored to employee database 152 and/or employee scheduling system 154. Employee availability can include employee shift preferences or scheduled vacation time, among other options.

In step 306, matching scheduler 100 creates employee combinations. Each employee combination created in step 306 includes at least one healthcare employee for which employee profile information was received in step 304. In some examples, the employee combinations created by matching scheduler 100 have particular numbers of certain types or classes of employees. For example, each employee combination can have a first number of doctors, a second number of nurses, a third number of janitors, and a fourth number of administrative employees. This example is intended to be illustrative and non-limiting, and in other examples different combinations of employees and employee quantity are possible. Matching scheduler 100 can query employee scheduling system to determine the classes and quantity of employees required for each class for the time period for which patient information was received in step 302. Additionally and/or alternatively, the classes and quantity of employees required for each class for given time periods can be stored to memory 104, and matching scheduler 100 can retrieve employee class and quantity information from memory 104. In at least some examples, the employee combinations of step 306 are all possible combinations of the healthcare employees available during the time period used in steps 302, 304 that conform the requirements for employee class and quantity. The employee combinations created in step 306 can be stored to memory 104 for further use with subsequent steps of method 300.

In step 308, matching scheduler 100 simulates predicted outcome scores for each employee combination created in step 306. Matching scheduler 100 includes one or more programs for scoring each employee combination according to the employee profiles for the employees of the combination and the patient health profiles for patients visiting the healthcare facility during the time period used in steps 302, 304. Matching scheduler 100 can include, for example, a computer-implemented machine learning model configured to evaluate combinations of healthcare employees and/or patients. The output of the computer-implemented machine learning model can reflect a predicted patient health outcome for one or more patients of the patients incoming during the time period used in steps 302, 304. In some examples, the computer-implemented machine learning model may be configured to accept patient health profile information for multiple patients and employee profile information for multiple healthcare employees as inputs. The patient health profile information can be the patient health profiles stored by patient database 142 and/or specific patient attributes of the patient health profiles stored by patient database 142. The employee profile information can be the employee profiles stored by employee database 152 and/or specific employee attributes of the employee profiles stored by employee database 152. In at least some of these examples, the computer-implemented machine learning model can accept as an input the patient health information for all patients expected to visit the healthcare facility during the time period used in steps 302, 304. In other examples, the computer-implemented machine learning model can be configured to only accept as an input one patient health profile, one employee profile, or both one patient health profile and one employee health profile. In these examples, matching scheduler 100 can be configured to, for each employee combination, score each employee and/or each patient using the machine learning model and to subsequently add the scores for each employee combination to create an overall patient output score for the employee combination.

Matching scheduler 100 can be configured to iteratively generate outcome scores for each employee combination using a simulator and the computer-implemented machine learning model. In some examples, the computer-implemented machine learning model may be configured to accept patient health profile information for multiple patients and employee profile information for multiple healthcare employees as inputs. In at least some of these examples, the computer-implemented machine learning model can accept as an input the patient health information for all patients expected to visit the healthcare facility during the time period used in steps 302, 304. In other examples, the computer-implemented machine learning model can be configured to only accept as an input one patient health profile, one employee profile, or both one patient health profile and one employee health profile. In these examples, matching scheduler 100 can be configured to, for each employee combination, score each employee and/or each patient using the machine learning model and to subsequently add the scores for each employee combination to create an overall patient output score for the employee combination.

The simulator can be configured to provide the correct quantity of employee profiles and patient health profiles to the computer-implemented machine learning model and to sum predicted outcome scores as required to create overall patient outcome scores for each employee combination. The simulator or another suitable program of matching scheduler 100 can further be configured to store the outputs of the computer-implemented machine learning model to memory 104 for use with further steps of method 300.

The computer-implemented machine learning model can be any suitable machine learning model and can be trained using historical patient outcome data and employee profile and patient health profile information. More specifically, patient health profile information (e.g., patient health attributes) for a given patient and healthcare employee profile information (e.g., employee attributes) for the healthcare employees working during the time period the patient visited a healthcare facility can be associated with a score that is assigned to reflect a health outcome for the patient. The score can, for example vary between zero and one and reflect an overall positivity of outcome. For example, a "1" can represent an ideal or most preferred outcome and a "0" can represent an unideal or least preferred outcome. The score can reflect or represent, among other options, an effectiveness of treatment or care received in alleviating a patent's symptoms or underlying condition, whether the patient required follow-up care for the same symptoms or underlying condition during a separate visit, and/or patient mortality rate following a visit. In some examples, the score can be normalized to reflect whether a patient's outcome is above or below average. The score can be normalized against average outcomes for patients seeking treatment for a particular affliction, disorder, disease, etc. For example, if the patient visited the healthcare facility seeking treatment for a particular type of viral infection, the patient's outcome can be scored against the average outcome of other patients seeking treatment for that type of viral infection. Additionally and/or alternatively, the patient's outcome can be normalized against other patients having similar biographical information or other medical information. As a specific example, a patient's outcome can be compared against outcomes for patient's having a similar age or similar pre-existing conditions, among other options.

In step 310, a preferred employee combination is selected. Matching scheduler 100 selects the preferred employee combination by comparing the patient outcome scores for each employee combination and determining which employee combination results in the highest overall score for the patients expected to visit the healthcare facility during the time period used in steps 302, 304. Where the computer-implemented machine learning model used in step 308 is configured to output individual patient outcome scores for each patient that are then subsequently summed, matching scheduler 100 can be configured to inspect individual patient outcome scores for employee combination in order to ensure that no individual patient outcome score is below a minimum acceptable patient outcome score. Matching scheduler 100 can exclude employee combinations that produce an individual patient outcome score below the minimum threshold score and to select from the remaining combinations the healthcare employee combination yielding the highest overall patient outcome score.

In step 312, matching scheduler 100 schedules healthcare employees of the preferred employee combination to work during the time period used in steps 302, 304. Step 312 is optional and can be performed where it is desirable for matching scheduler 100 to modify employee scheduling system 154 in response to the determination made in step 310. Matching scheduler 100 can automatically modify the data stored to employee scheduling system 154 and/or can cause employee scheduling system 154 to automatically identify stored scheduling data in order to schedule the healthcare employees of the preferred employee combination. In at least some examples, matching scheduler 100 can be configured to automatically schedule the healthcare employees in response to selecting the preferred employee combination in step 310. In examples of method 300 that omit step 312, matching scheduler 100 can output the preferred employee combination to allow a user to subsequently modify employee scheduling system 154 to schedule the preferred employee combination. In yet further examples, matching scheduler 100 can store the preferred employee combination to memory 104 and employee scheduling system 154 can be configured to query matching scheduler 100 to retrieve the preferred employee combination.

As depicted in FIG. 2, steps 302-310 and/or steps 302-312 can be performed iteratively to create employee schedules for multiple time periods, shifts, or appointment windows. Method 300 can be iterated to create employee schedules and, in some examples, to schedule employees for as many time periods, shifts, or appointment windows as is desirable. In some examples, method 300 can be iterated for individual employee classes. For example, a first iteration of method 300 can be used to schedule doctors, a second iteration of method 300 can be used to schedule nurses, a third iteration of method 300 can be used to schedule administrative employees, etc. In at least some examples, the shifts or time periods scheduled using method 300 overlap. As referred to herein, two time periods "overlap" if at least part of each shift occurs at the same or substantially the same time. Advantageously, this allows method 300 to be used to schedule employees in complex hospital environments where different classes of employees may work different but overlapping shifts. Further, it may be advantageous for employee shifts to partially overlap during a shift change in order to improve, for example, workplace safety or patient safety, among other options, during the shift change.

Method 300 advantageously allows for the employees working during a given shift, time period, or appointment window to be personalized and selected based on traits of patients expected to visit during that shift, time period, or appointment window and further based on the traits of available employees. Method 300 further leverages associations made using machine learning models to select employees in order to adjust and/or improve outcomes and, in some examples, patient experience for a specific, expected patient population. Method 300 can be used not only to predictively select medical employees to adjust and/or improve patient outcomes, but can also be used to predictively select non-medical employees to work during a particular shift, time period, or appointment window in order to adjust and/or improve patient outcomes. Accordingly, method 300 advantageously can adjust and/or improve patient outcomes and, in some examples, improve patient retention by adjusting and/or improving patient experience at a healthcare facility.

Figure 3:
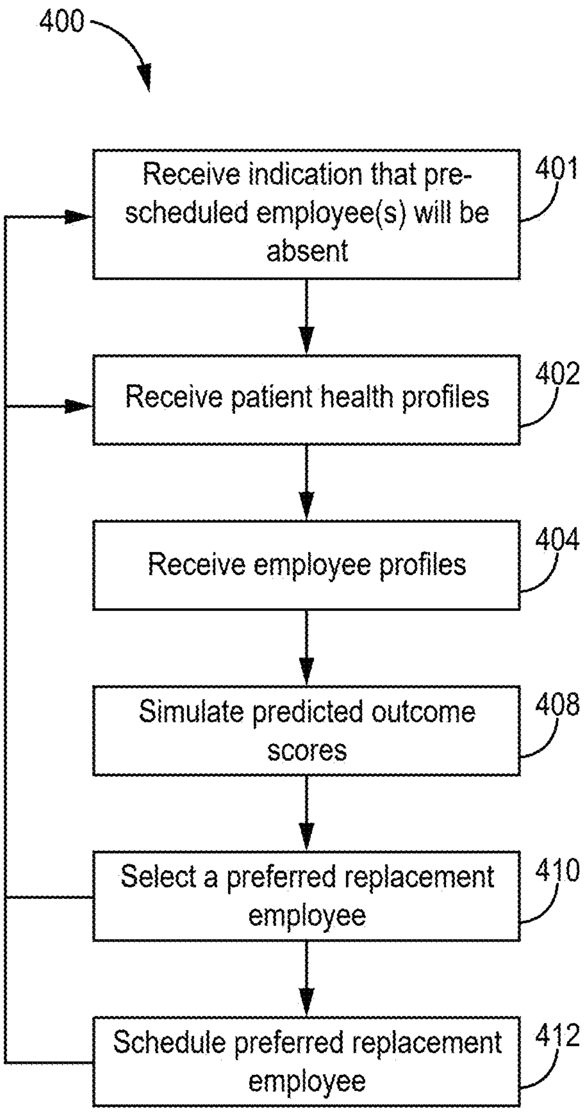
FIG. 3 is a flow diagram of an example of a method of rescheduling healthcare employees suitable for use by the system of FIG. 1

FIG. 3 is a flow diagram of method 400, which is a method of modifying an existing employee schedule for a shift at a healthcare facility. Method 400 includes steps 401-412 of receiving an indication that one or more pre-scheduled employees will be absent from a shift (step 401), receiving patient health profiles (step 402), receiving employee profiles (step 404), simulating predicted outcome scores (step 408), selecting a preferred replacement employee (step 410), and scheduling the preferred replacement employee (step 412). Method 400 can be performed by matching scheduler 100 to schedule employees of hospital system 182 and/or any healthcare facility 180A-N. Method 400 is performable by, for example, one or more programs of rescheduling module 130. Method 400 will be discussed generally herein with reference to matching scheduler 100 for simplicity clarity, but method 300 can be performed by any suitable hardware device to create employee schedules for a healthcare facility.

As will be explained in more detail subsequently, method 400 can be performed to schedule a replacement employee when another employee is unable to work a scheduled shift. For example, a previously-scheduled employee may call out sick or otherwise be able to report to work for a scheduled shift. To avoid undesirable understaffing during the shift, another employee is that is not already scheduled during the shift and is otherwise able to work (e.g., the employee is able to commute to the facility, an additional shift would not violate relevant labor laws, etc.), can be scheduled to cover the missed shift on relatively short notice. Typically, method 400 is performed to fill gaps in understaffed shifts on less notice than is typically provided to employees of the healthcare facility. To this extent, while method 300 can be performed to create schedules on regular intervals, as described previously, method 400 performs rescheduling operations when it is known that an employee will not be present for a given shift.

In step 401, matching scheduler 100 receives an indication that one or more pre-scheduled employees will be absent from a shift for which those employee(s) were scheduled. As referred to herein, a "pre-scheduled employee" is an employee that has been previously scheduled to work a particular shift. The shift for which a pre-scheduled employee will be absent is referred to herein as an "understaffed shift." The healthcare facility 180A-N at which the understaffed shift is scheduled to occur is referred to herein as an "understaffed healthcare facility." Matching scheduler 100 can receive the indication from, for example, employee scheduling system 154 and/or by input at user interface 106 or another user interface of scheduling system 10. The indication includes identifying information (e.g., a name, identification number, etc.) for the employee that will miss a shift and the time during which the shift is scheduled to occur. Accordingly, step 401 allows matching scheduler 100 to identify the shift for which a replacement employee is required as well as which employee will not be able to be present during the shift. Steps 402-412 can be performed iteratively, simultaneously, and/or substantially simultaneously for each employee and shift identified in step 401, as indicated by the arrows shown in FIG. 3.

In step 402, matching scheduler 100 receives patient health profiles for patients scheduled to visit the understaffed healthcare facility 180A-N during the scheduled shift. Step 402 can be performed in substantially the same manner as step 302 (FIG. 2) and the description of step 302 herein is also applicable to step 402.

In step 404, matching scheduler 100 receives employee profiles for employees available to work during the understaffed shift identified in step 401. Step 404 can be performed in substantially the same manner as step 304 (FIG. 2) and the description of step 304 herein is also applicable to step 404. In some examples, the employee profiles selected in step 404 can belong to, for example, employees of the same class as the pre-scheduled employee identified in step 401. For example, matching scheduler 100 can query employee database 152 with identification for the pre-scheduled employee to determine the class that employee belongs to, and use that class to query employee database 152 in order to determine which employees are suitable replacement employees.

In step 408, matching scheduler 100 creates predicted outcome scores for each potential replacement employee. As referred to herein, a "potential replacement employee" is any employee able to work during the understaffed shift identified in step 401 and, if required, belonging to the same class as the pre-scheduled employee identified in step 401. The pool of potential replacement employees can be identified in step 404 from the data stored to employee database 154. Step 408 can be performed in substantially the same manner as step 308 (FIG. 2) and the description of step 308 herein is also applicable to step 408. Step 408 can also be performed using the computer-implemented machine learning model(s) trained to predict patient outcomes based on patient health profile and employee profile information described previously with respect to step 308. For each potential replacement employee, matching scheduler 100 can create a predicted outcome score using the employee profile for the potential replacement employee and the patient profiles received in step 402. As described previously, if a computer-implemented machine learning model that is trained to output scores on a patient-by-patient basis is used (i.e., such that separate outcomes scores are calculated for each patient of the group of patients scheduled during the understaffed shift identified in step 401), matching scheduler 100 can be configured to sum patient scores for the shift to create an overall patient outcome score, and further can be configured to exclude potential replacement employees that produce a score for any patient below a given threshold value.

In step 410, matching scheduler 100 selects a preferred replacement employee based on the predicted outcome scores generated in step 408. Step 410 can be performed in substantially the same manner as step 310 (FIG. 2) and the description of step 310 herein is also applicable to step 410. In step 412, the preferred replacement employee is scheduled to work the understaffed shift identified in step 401 (i.e., the shift for which the pre-scheduled employee was originally assigned to work). Step 412 can be performed in substantially the same manner as step 312 (FIG. 2) and the description of step 312 herein is also applicable to step 412.

In some examples, step 408 may be performed using a machine learning model configured to accept employee profile information for more than one employee as an input. In these examples, employee profiles for the other employees scheduled to work during the understaffed shift at the healthcare facility 180A-N can be received in step 404 and employee combinations can be made prior to calculation of predicted outcome scores in step 408. The employee combinations can include all other employees scheduled to work during the understaffed shift (i.e., other than the pre-scheduled employee expected to be absent) and one potential replacement employee. A predicted outcome score can be generated for each employee combination and the preferred employee combination can be selected based on the predicted outcome scores. In these examples, the preferred replacement employee selected in 410 is the potential replacement employee of the preferred employee combination.

As depicted in FIG. 3, steps 401-410, 401-412, 402-410, and/or 402-412 can be performed iteratively to reschedule employees to cover understaffed shifts. Method 400 can be iterated on a schedule or in particular time increments in order to check for expected employee absences and to reschedule employees appropriately. Matching scheduler 100 can also be configured to passively receive indications that employees will be absent from particular shifts from one or more other components of scheduling system 10 (i.e., step 401) and to automatically subsequent steps of method 400 in response to the received indication.

Method 400 advantageously allows for the employees scheduled to cover an absence during a given shift to be personalized and selected based both on traits of patients expected to visit during that shift based and on the traits of available employees. Method 400 further leverages associations made using machine learning models to select replacement employees in order to adjust and/or improve outcomes and, in some examples, patient experience for a specific, expected patient population. Accordingly, like method 300, method 400 can advantageously adjust and/or improve patient outcomes and, in some examples, adjust and/or improve patient retention by improving patient experience at a healthcare facility. Method 400 can be used to select employees to cover shifts for both medical and non-medical employee absences in order to adjust and/or improve patient outcomes. In some examples, it may not be appropriate to perform method 400 for all employees. For example, if a patient specifically schedules an appointment with a primary care physician, it may be undesirable or a violation of relevant regulations or laws to reschedule that primary care doctor without also rescheduling the patients planning on receiving care from the primary care doctor during the shift for which the primary care doctor is not able to work. In these examples, method 400 can be limited to rescheduling employees other than primary care physicians, such as nurses, secondary physicians, administrative staff, janitorial staff, maintenance staff, etc.

Method 400 has been discussed herein generally with respect to modifying a shift schedule to include an employee that was not previously scheduled to work during the understaffed shift. In some examples, there may be no available employees that are not already scheduled for a shift during the understaffed shift. In these examples, matching scheduler 100 can perform method 450. Method 450 is substantially similar to method 400, but includes additional steps that allow matching scheduler 100 to evaluate the impact of removing an employee from a currently-scheduled shift in order to reschedule that employee at an already-understaffed healthcare facility. Method 450 includes steps 451-462 of receiving an indication that one or more pre-scheduled employees will be absent from a shift (step 451), receiving patient health profiles for the understaffed healthcare facility (step 452), receiving employee profiles (step 454), receiving patient health profiles for patients of other healthcare facilities of a hospital system (step 455), simulating predicted outcome scores (step 458), selecting a preferred replacement employee (step 460), and scheduling the preferred replacement employee (step 462). Method 400 can be performed by matching scheduler 100 to schedule employees of hospital system 182 and/or any healthcare facility 180A-N. Method 400 is performable by, for example, one or more programs of rescheduling module 130. Method 400 will be discussed generally herein with reference to matching scheduler 100 for simplicity clarity, but method 300 can be performed by any suitable hardware device to create employee schedules for a healthcare facility.

In step 451, matching scheduler 100 receives an indication that one or more pre-scheduled employees will be absent from a shift for which those employee(s) were scheduled. Step 451 is substantially the same as step 401 of method 400 (FIG. 4), and the description of step 401 of method 400 is applicable to step 451 of method 450. The indication received in step 451 can also include the healthcare facility 180A-N of hospital system 182 at which the pre-scheduled employee was expected to work (i.e., the identity of the understaffed healthcare facility 180A-N). Additionally and/or alternatively, matching scheduler 100 can query employee scheduling system 154 to determine at which healthcare facility 180A-N the pre-scheduled employee was expected to work. Similarly to steps 402-412 of method 400 (FIG. 3), Steps 452-462 can be performed iteratively, simultaneously, and/or substantially simultaneously for each employee and shift identified in step 451, as indicated by the arrows shown in FIG. 4.

In step 452, matching scheduler 100 receives patient health profiles for patients expected to visit the understaffed healthcare facility during the understaffed shift. Step 452 is substantially the same as step 402 of method 400, and the description of step 402 of method 400 is applicable to step 452 of method 450.

In step 454, matching scheduler 100 receives employee profiles for employees currently scheduled at other healthcare facilities 180A-N during the understaffed shift. Step 454 can be performed in substantially the same manner as step 404 (FIG. 3) and the description of step 404 herein is also applicable to step 454. In step 455, matching scheduler receives patient health profiles for the patients scheduled or expected to visit other healthcare facilities 180A-N of hospital system 182 during the scheduled shift (i.e., other than the understaffed healthcare facility identified in step 151) and who are additionally expected to visit a healthcare facility 180A-N at which the potential replacement employees are already scheduled to work during the understaffed shift. Step 455 is substantially similar to step 452 and can be performed in substantially the same manner as step 452. Obtaining patient health profile information for patients visiting the facilities where the potential replacement employees are scheduled during the understaffed shift allows the relative impact of rescheduling each potential replacement employee on all potentially affected patients of hospital system 182 to be predicted.

In step 458, predicted outcome scores are simulated for each potential replacement employee identified in step 454. Matching scheduler 100 creates two predicted outcome scores for each potential replacement employee. Specifically, matching scheduler creates a first outcome score that describes the predicted patient outcomes for patients expected to visit the healthcare facility at which the pre-scheduled employee will be absent (i.e., the patients for which profile information was received in step 452) and a second outcome score that describes the predicted patient outcomes for patients expected to visit the healthcare facility at which the potential replacement employee was originally scheduled to work during the understaffed shift (i.e., the patients for which profile information was received in step 455). Step 458 can be performed in substantially the same manner as described previously with respect to step 408 of method 400 (FIG. 4) and step 308 of method 300 (FIG. 2). Step 458 can also be performed using the computer-implemented machine learning model(s) trained to predict patient outcomes based on patient health profile and employee profile information described previously with respect to steps 308, 408.

In step 460, matching scheduler 100 selects a preferred replacement employee based on the predicted outcome scores generated in step 458. Matching scheduler 100 can compare the two predicted outcome scores generated in step 458 to determine an overall or net impact predicted to result in rescheduling the potential replacement employee. As a specific example, matching scheduler 100 can, for example, compare the predicted outcome scores by determining the difference between the predicted outcome scores and storing that value as the net outcome score for the employee. Matching scheduler 100 can then select the potential replacement employee having the greatest net outcome score as the potential replacement employee. If the net outcome score for no employee is positive (i.e., such the predicted increase in patient outcome positivity at the understaffed healthcare facility 180A-N is less than the concomitant decrease in patient outcome positivity at the healthcare facility 180A-N at which the potential replacement employee is already scheduled), matching scheduler 100 can be configured to stop performing method 450 and not select a preferred replacement employee.

In step 462, matching scheduler 100 schedules the preferred replacement employee to work at the understaffed healthcare facility during the understaffed shift. Matching scheduler 100 can modify employee scheduling system 154 to adjust the preferred replacement employee's schedule or cause employee scheduling system 154 to adjust the preferred replacement employee's schedule. Employee scheduling system 154 can be modified to schedule the preferred replacement employee at the understaffed healthcare facility and to remove the preferred replacement employee from the schedule at the healthcare facility 180A-N at which the preferred replacement employee was originally scheduled to work during the understaffed shift. Similar to step 412 (FIG. 3) and step 312 (FIG. 2), step 462 is optional and can be performed where it is desirable for matching scheduler 100 to modify employee scheduling system 154 in response to the determination made in step 460. In at least some examples, matching scheduler 100 can be configured to automatically schedule the healthcare employees in response to selecting the preferred replacement employee in step 460. In examples of method 4500 that omit step 462, matching scheduler 100 can output the preferred replacement employee to allow a user to subsequently modify employee scheduling system 154 to schedule the preferred replacement employee. In yet further examples, matching scheduler 100 can store the preferred replacement employee to memory 104 and employee scheduling system 154 can be configured to query matching scheduler 100 to retrieve the preferred replacement employee.

As depicted in FIG. 3, steps 451-460, 451-462, 452-460, and/or 452-462 can be performed iteratively to reschedule employees to cover understaffed shifts. Method 400 can be iterated on a schedule or in particular time increments in order to check for expected employee absences and to reschedule employees appropriately. Matching scheduler 100 can also be configured to passively receive indications that employees will be absent from particular shifts from one or more other components of scheduling system 10 (i.e., step 401) and to automatically subsequent steps of method 400 in response to the received indication.

Method 450 provides substantially the same advantages as discussed previously with respect to method 400. Accordingly, like method 400 and method 300, method 450 can advantageously be used to adjust and/or improve patient outcomes when rescheduling employees and further, in some examples, can adjust and/or improve patient experience when employees are rescheduled. Similarly, like method 400 and method 300, method 450 can be used to shift both medical and non-medical employees to cover understaffed shifts. Like method 400, it may not be appropriate to perform method 450 to reschedule all classes of employees, such as primary care physicians. In these examples, matching scheduler 100 can be configured to perform method 450 to reschedule only certain classes of employees.

Figure 5:
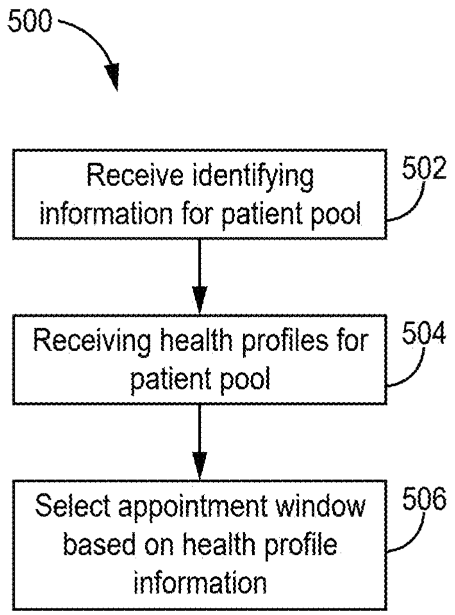
FIG. 5 is a flow diagram of an example of a method of generating preferred appointment windows based on patient information.

FIG. 5 is a flow diagram of method 500, which is a method of scheduling patients suitable for use with matching scheduler 100, patient scheduling system 144, or another suitable component of scheduling system 10. FIG. 5 includes steps of receiving identifying information for an incoming pool of patients (step 502), receiving health profiles for the patient pool (step 504), and selecting appointment windows for the patients based on the health profile information (step 506). Method 500 is optional and can be performed independently of methods 300, 400, 450. Method 500 allows scheduling system 100 to determine times of day associated with improved patient outcomes. Certain patients may have an improved experience and therefore be more likely to follow medical care or treatment instructions if they visit at a particular time of day, such as the morning, the afternoon, early evening, evening, etc. Method 500 will be discussed generally herein with reference to matching scheduler 100 for simplicity and clarity, but method 500 can be performed by any suitable hardware device to create relationships between appointment times and patient outcomes.

In step 502, matching scheduler 100 receives identifying information for an incoming pool of patients. The patients of the incoming pool of patients have not yet been scheduled to visit a healthcare facility 180A-N. Patient scheduling system 144 or another element of scheduling system 10 can store a list of patients that are due to visit a healthcare facility 180A-N. Matching scheduler 100 can query patient scheduling system 144 or the other element of scheduling system 10 to receive identifying information for the incoming pool of patients.

In step 504, matching scheduler 100 receives health profile information for the incoming patient pool for which identifying information was received in step 502. Matching scheduler 100 can receive the health profile information by, for example, querying patient database 142 with the identifying information received in step 502.

In step 506, matching scheduler 100 selects a preferred appointment window for each patients the health profile information received in step 504. In some examples, matching scheduler 100 can use a computer-implemented machine learning model configured to output a preferred appointment time based on patient health profile information. The model can be trained using a data set of preferred appointment times and patient health profiles. In yet further examples, matching scheduler 100 can use a computer-implemented machine learning model configured to output a predicted patient outcomes score based on time of day and patient health profile information. The computer-implemented machine learning model can be trained using patient health profile data (e.g., patient health attributes) and time of day data labeled with patient outcome scores. The patient outcome scores can represent, for example, an effectiveness of treatment or care received in alleviating a patent's symptoms or underlying condition, whether the patient required follow-up care for the same symptoms or underlying condition during a separate visit, and/or patient mortality rate following a visit. The time of day information used by the computer-implemented machine learning model can be specific times of day, specific windows of time, and/or more generalized time window information, such as whether an appointment occurred during the morning, afternoon, or evening. Matching scheduler 100 can perform step 506 for each patient of the incoming patient pool and use the outputs from the computer-implemented machine learning model used in step 506 to determine a preferred appointment window for each patient. Matching scheduler 100 can output the preferred appointment window as, for example, text or image data to an employee of hospital system 182. The employee of hospital system 182 can then schedule patients of the incoming patient pool to specific appointments using the output data. In other examples, matching scheduler 100 can modify patient scheduling system 142 to schedule patients of the incoming patient pool or otherwise cause patient scheduling system 142 to schedule patients of the incoming patient pool according to the appointment windows created in step 506.

Method 500 advantageously allows for patients visiting a healthcare facility 180A-N to be scheduled to an appointment that is more likely to result in a positive medical outcome. Some patients may be less receptive to medical advice or less likely to remember doctor or provider instructions given during appointments at certain times of day, among other impacts on patient outcomes. The effect of appointment time on patient outcomes that can be captured in the patient outcome scores or preferred appointment times output used to train the computer-implemented machine learning model used in step 506.

Figure 6:
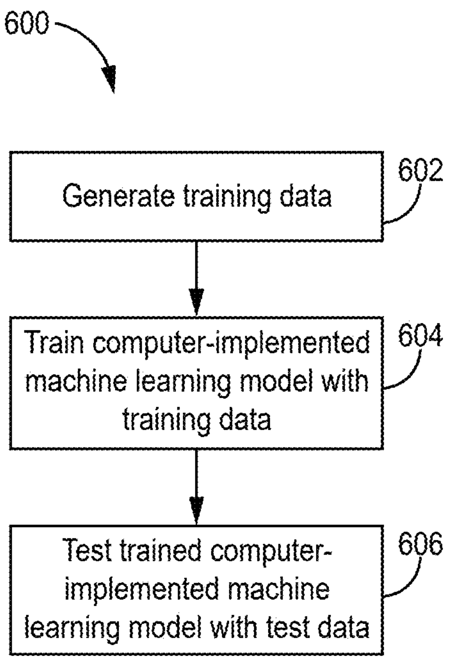
FIG. 6 is a flow diagram of an example of a method of a method of training a machine learning algorithm to create predictive staffing models for use with the methods of FIGS. 2-5.

FIG. 6 is a flow diagram of method 600, which is a method of training a machine learning algorithm described herein, such as a machine learning algorithm for creating predicted patient outcome scores (e.g., methods 300, 400, 450, 500) or creating preferred patient appointment windows (e.g., method 500). Method 600 includes steps of generating training data (step 602), training the computer-implemented machine learning model with the training data (step 604), and testing the trained computer-implemented machine learning model with test data (step 606). Method 600 is a method of supervised learning that can be used to train any suitable computer-implemented machine learning model for use with any of methods 300, 400, 450, 500.

In step 602, the training data is generated. For training the computer-implemented machine learning model(s) used in method 300, 400, 450, training data includes patient profile information paired with or otherwise associated with employee profile information for the employees that worked during the times that the patients received medical care at a healthcare facility. The training data is labeled with a patient outcome score, as described previously. The patient outcome scores can be manually generated based on patient outcomes following the visit to the healthcare facility. Patient outcome can be assessed based on, for example, an effectiveness of treatment or care received in alleviating a patent's symptoms or underlying condition, whether the patient required follow-up care for the same symptoms or underlying condition during a separate visit, and/or patient mortality rate following a visit, and can be represented as a value varying between 0 and 1, among other options. For training the computer-implemented machine learning model(s) used in method 500, the training data can be patient profile information labeled with a preferred appointment window. Alternatively, the training data can also be patient profile information and time of day information labeled with a patient outcome score, as described elsewhere herein.

In step 604, the labeled data is used to train the computer-implemented machine learning model to predict numbers of missed bags based on driver quantities and flight parameters. As used herein, "training" a computer-implemented machine learning model refers to any process by which parameters, hyper parameters, weights, and/or any other value related model accuracy are adjusted to improve the fit of the computer-implemented machine learning model to the training data. The labeled data can be transformed by, for example, one or more programs and/or one or more other trained machine learning models before it is used for training in step 604.

In step 606, the trained computer-implemented machine learning model is tested with test data. The test data used in step 606 is not used during training in step 604 and may optionally be labeled in the same manner as the labeled data used in step 604, but otherwise is substantially the same type of data as used in step 604. Accordingly, the test data is unlabeled data that can be used to qualify and/or quantify performance of the trained computer-implemented machine learning model. More specifically, a human or machine operator can evaluate the performance of the machine learning model by evaluating the fit of the model to the test data. Step 606 can be used to determine, for example, whether the machine learning model was overfit to the labeled data during model training in step 604.

Figure 4:
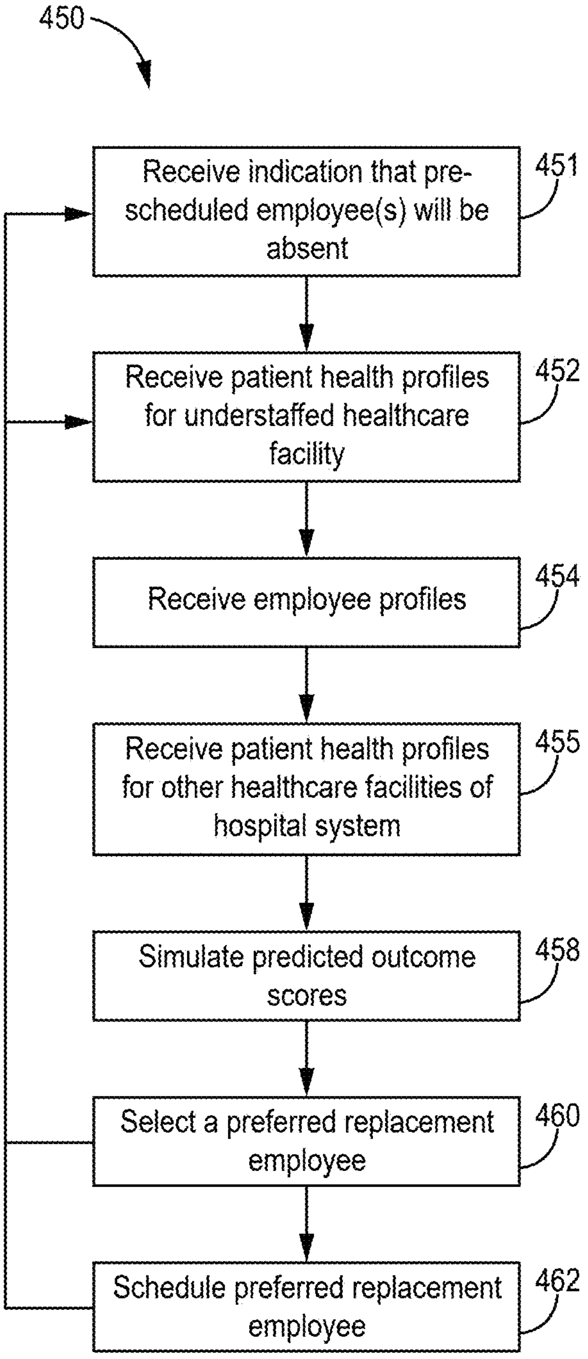
FIG. 4 is a flow diagram of another example of a method of rescheduling healthcare employees suitable for use by the system of FIG. 1

As depicted in FIG. 4, steps 604 and 606 can be performed iteratively to improve the performance of the machine learning model. More specifically, if the fit of the model to the test data determined in step 606 is undesirable, step 606 can be repeated to further adjust the parameters, hyper parameters, weights, etc. of the model to improve the fit of the model to the test data. Step 606 can then be repeated with the same set and/or a new set of test data to determine how the adjusted model fits the test data. If the fit continues to be undesirable, further iterations of steps 604 and 606 can be performed until the fit of the model becomes desirable.

Method 600 can advantageously be used to train any machine learning model described herein. More generally, the systems and methods disclosed herein advantageously allow for the training and use of machine learning models that can be used to predict patient outcomes with various employees. The systems and methods disclosed herein can also be used to select patient appointment times associated with improved patient outcomes. As described previously, the systems and methods disclosed herein can also be used to adjust and/or improve patient experience, which can improve patient outcome and further can improve patient retention at a given healthcare facility.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method of creating a healthcare employee schedule, the method comprising:

generating a labeled training data set comprising a plurality of employee-patient profile training combinations labeled with patient outcome scores, wherein each employee-patient profile training combinations including at least one training employee profile and one training patient profile, each training employee profile comprising one set of employee attributes and each training patient profile comprising one set of patient health attributes;

training a first computer-implemented machine-learning model by fitting parameters of the computer-implemented machine-learning model to the labeled training data set, thereby generating a first trained-computer implemented machine-learning model for predicting patient outcome scores based on input features comprising:

employee attributes from employee profiles; and patient health attributes from patient health profiles;

receiving a first plurality of patient health profiles for a first plurality of patients, each patient health profile of the first plurality of patient profiles comprising patient health attributes for one patient of the first plurality of patients, the first plurality of patients expected to visit a healthcare facility during a first time period;

receiving a first plurality of employee profiles for a first plurality of healthcare employees, each employee profile for the first plurality of healthcare employees corresponding to one healthcare employee of the first plurality of healthcare employees, wherein:

the healthcare employees of the first plurality of healthcare employees belong to a first class of healthcare employees; and each employee profile of the first plurality of employee profiles comprises at least one employee attribute;

creating a first plurality of employee combinations, each employee combination of the first plurality of employee combinations including at least two healthcare employees of the first plurality of healthcare employees;

simulating, for each employee combination, a first predicted outcome score using a simulator, a first trained computer-implemented machine learning model, the first plurality of patient health profiles, and employee profiles of the first plurality of employee profiles corresponding to the healthcare employees of the employee combination, the first predicted outcome score describing a health outcome for the first plurality of patients;

selecting a first preferred employee combination of the plurality of predicted employee combinations based on the simulated first predicted outcome scores; and in response to selecting the first preferred employee combination, automatically modifying electronic data of an electronic employee scheduling system to schedule of the first preferred employee combination during the first time period.

2. The method of claim 1, and further comprising receiving a first staffing quantity for the first time period, wherein:

the first staffing quantity is a preferred quantity of the first class of healthcare employees; and each employee combination of the first plurality of employee combinations includes the first staffing quantity of healthcare employees of the first plurality of healthcare employees.

3. The method of claim 2, and further comprising receiving a second plurality of employee profiles for a second plurality of healthcare employees, each employee profile for the second plurality of healthcare employees corresponding to one healthcare employee of the second plurality of healthcare employees, wherein:

the healthcare employees of the second plurality of healthcare employees belong to a second class of healthcare employees;

each employee profile of the second plurality of employee profiles comprises at least one employee attribute; and each employee combination of the first plurality of employee combinations includes at least one healthcare employee of the second plurality of healthcare employees.

4. The method of claim 3, and further comprising receiving a second staffing quantity for the first time period, wherein:

the second staffing quantity is a preferred quantity of the second class of healthcare employees; and each employee combination of the first plurality of employee combinations includes the second staffing quantity of healthcare employees of the second plurality of healthcare employees.

5. The method of claim 4, and further comprising receiving a third plurality of employee profiles for a third plurality of healthcare employees, each employee profile for the third plurality of healthcare employees corresponding to one healthcare employee of the third plurality of healthcare employees, wherein:

the healthcare employees of the third plurality of healthcare employees belong to a third class of healthcare employees;

each employee profile of the third plurality of employee profiles comprises at least one employee attribute; and each employee combination of the first plurality of employee combinations includes at least one healthcare employee of the third plurality of healthcare employees.

6. The method of claim 5, and further comprising receiving a third staffing quantity for the first time period, wherein:

the third staffing quantity is a preferred quantity of the third class of healthcare employees; and each employee combination of the first plurality of employee combinations includes the third staffing quantity of healthcare employees of the third plurality of healthcare employees.

7. The method of claim 6, wherein:

the first class of employees are caregivers;

the second class of employees are administrative staff; and the third class of employees are facilities maintenance staff.

8. The method of claim 7, wherein the first plurality of patient profiles comprises electronic health records for the first plurality of patients.

9. The method of claim 8, and further comprising receiving a plurality of patient identifying information for the first plurality of patients, and wherein receiving the first plurality of patient health profiles comprises querying a patient health profile database with the plurality of patient identifying information.

10. The method of claim 9, and further comprising scheduling the first plurality of patients for a plurality of appointments at the healthcare facility during the first time period.

11. The method of claim 10, wherein scheduling the first plurality of patients comprises:

receiving identifying information of a pool of incoming patients, the first plurality of patients belonging to the pool of incoming patients;

querying the health record database with the identifying information of the pool of incoming patients to receive patient health profiles for the pool of incoming patients; and selecting the first plurality of patients from the pool of incoming patients based on the first time period and the patient health profiles for the pool of incoming patients.

12. The method of claim 11, wherein selecting the first plurality of patients from the pool of incoming patients comprises:

generating a plurality of patient outcome scores for the pool of incoming patients using a second computer-implemented machine learning model, the patient health profiles, and the first time period, wherein:

the second computer-implemented machine learning model is configured to output patient outcome scores based on patient health profiles and appointment times; and each patient outcome score for the pool of incoming patients represents an outcome positivity for one patient of the pool of incoming patients associated with the first time period; and selecting the first plurality of patients from the pool of incoming patients based on the plurality of patient outcome scores.

13. The method of claim 1, and further comprising selecting the first plurality of healthcare employees from a pool of healthcare employees of the first class of healthcare employees based on employee availability during the first time period.

14. The method of claim 13, and further comprising:

selecting a second plurality of healthcare employees from the pool of healthcare employees based on employee availability during a second time period, the second time period different from the first time period;

receiving a second plurality of patient health profiles for a second plurality of patients, each patient health profile of the second plurality of patient health profiles corresponding to one patient of the second plurality of patients, the second plurality of patients expected to visit the healthcare facility during the second time period;

receiving a second plurality of employee profiles for the second plurality of healthcare employees, each employee profile for the second plurality of healthcare employees corresponding to one healthcare employee of the second plurality of healthcare employees, wherein:

the healthcare employees of the second plurality of healthcare employees belong to the first class of healthcare employees; and each employee profile of the second plurality of employee profiles comprises at least one employee attribute;

creating a second plurality of employee combinations, each employee combination of the second plurality of employee combinations including at least two healthcare employees of the second plurality of healthcare employees;

simulating, for each employee combination of the second plurality of employee combinations, a second predicted outcome score using a simulator, the computer-implemented machine learning model, patient health profiles for the second plurality of patients, and employee profiles for the healthcare employees of the employee combination;

selecting a second preferred employee combination of the second plurality of employee combinations simulated second predicted outcome scores; and scheduling healthcare employees of the first preferred employee combination during the second time period.

15. The method of claim 14, wherein the first time period overlaps the second time period.

16. A system comprising:

a patient database;

an employee database;

an electronic employee scheduling system;

a processor; and computer-readable memory encoded with instructions that, when executed, cause the processor to:

retrieve a labeled training data set comprising a plurality of employee-patient profile training combinations labeled with patient outcome scores, wherein each employee-patient profile training combinations including at least one training employee profile and one training patient profile, each training employee profile comprising one set of employee attributes and each training patient profile comprising one set of patient health attributes;

train a first computer-implemented machine-learning model by fitting parameters of the computer-implemented machine-learning model to the labeled training data set, thereby generating a first trained-computer implemented machine-learning model for predicting patient outcome scores based on input features comprising:

employee attributes from employee profiles; and patient health attributes from patient health profiles;

receive, from the patient database, a first plurality of patient health profiles for a first plurality of patients, each patient health profile of the first plurality of patient profiles comprising patient health attributes for one patient of the first plurality of patients, the first plurality of patients expected to visit a healthcare facility during a first time period;

receive, from the employee database, a first plurality of employee profiles for a first plurality of healthcare employees, each employee profile for the first plurality of healthcare employees corresponding to one healthcare employee of the first plurality of healthcare employees, wherein:

the healthcare employees of the first plurality of healthcare employees belong to a first class of healthcare employees; and each employee profile of the first plurality of employee profiles comprises at least one employee attribute;

create a first plurality of employee combinations, each employee combination of the first plurality of employee combinations including at least two healthcare employees of the first plurality of healthcare employees;

simulate, for each employee combination, a first predicted outcome score using a simulator, a first computer-implemented machine learning model, patient health profiles for the first plurality of patients, and employee profiles for the healthcare employees of the employee combination;

select a first preferred employee combination of the plurality of predicted employee combinations based on the simulated first predicted outcome scores; and responsive to selecting the first preferred employee combination, automatically modify electronic data of the electronic employee scheduling system to schedule healthcare employees of the first preferred employee combination during the first time period.

17. The system of claim 16, wherein the instructions, when executed, further cause the processor to receive, from the electronic employee scheduling system, a first staffing quantity for the first time period, wherein:

the first staffing quantity is a preferred quantity of the first class of healthcare employees; and each employee combination of the first plurality of employee combinations includes the first staffing quantity of healthcare employees of the first plurality of healthcare employees.

18. The system of claim 16, wherein the instructions, when executed, further cause the processor to receive, from the employee database, a second plurality of employee profiles for a second plurality of healthcare employees, each employee profile for the second plurality of healthcare employees corresponding to one healthcare employee of the second plurality of healthcare employees, wherein:

the healthcare employees of the second plurality of healthcare employees belong to a second class of healthcare employees;

each employee profile of the second plurality of employee profiles comprises at least one employee attribute; and each employee combination of the first plurality of employee combinations includes at least one healthcare employee of the second plurality of healthcare employees.

* * * * *